(12) United States Patent
Zhang (10) Patent No.: US 10,874,399 B2
(45) Date of Patent: Dec. 29, 2020

(54) CIRCULAR STAPLER WITH VISUAL INDICATOR MECHANISM

(71) Applicant: Covidien LP, Mansfield, MA (US)

(72) Inventor: Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 152 days.

(21) Appl. No.: 16/073,354

(22) PCT Filed: Feb. 4, 2016

(86) PCT No.: PCT/CN2016/073471
§ 371 (c)(1),
(2) Date: Jul. 27, 2018

(87) PCT Pub. No.: WO2017/132932
PCT Pub. Date: Aug. 10, 2017

(65) Prior Publication Data
US 2019/0038292 A1 Feb. 7, 2019

(51) Int. Cl.
*A61B 17/115* (2006.01)
*A61B 17/072* (2006.01)
*A61B 90/00* (2016.01)

(52) U.S. Cl.
CPC ........ *A61B 17/1155* (2013.01); *A61B 17/072* (2013.01); *A61B 2017/07257* (2013.01); *A61B 2090/0811* (2016.02)

(58) Field of Classification Search
CPC .............. A61B 17/1155; A61B 17/072; A61B 2017/07257; A61B 2090/0811
USPC .......................................... 227/175.1–182.1
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Japanese Office Action dated Sep. 10, 2019, issued in JP Application No. 2018-537847 (English translation not available).

(Continued)

*Primary Examiner* — Robert F Long
(74) *Attorney, Agent, or Firm* — Carter, DeLuca & Farrell LLP (57) ABSTRACT

A surgical stapling device includes a visual indicator mechanism that provides a clinician with greater visualization of the movement of an anvil assembly in relation to a cartridge assembly after the anvil and cartridge assemblies have been approximated to within a firing zone. The visual indicator mechanism improves visualization of the different degrees of approximation within the firing zone by providing an indicator cover having spaced slots that allow indicia formed on an indicator member to sequentially appear within the spaced slots to identify the different degrees of approximation within the firing zone.

14 Claims, 5 Drawing Sheets

(56) References Cited

U.S. PATENT DOCUMENTS

| | | |
|---|---|---|
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,527,724 A * | 7/1985 | Chow .................. A61B 17/072 227/8 |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,441,191 A * | 8/1995 | Linden .................. B25C 5/1689 227/120 |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,478,003 A * | 12/1995 | Green .............. A61B 17/07207 227/176.1 |
| 5,497,934 A | 3/1996 | Brady et al. |
| 5,503,635 A | 4/1996 | Sauer et al. |
| 5,507,425 A * | 4/1996 | Ziglioli .................. B25C 5/1689 116/278 |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |

(56) References Cited

U.S. PATENT DOCUMENTS

| | | |
|---|---|---|
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,464,847 B2 * | 12/2008 | Viola .............. A61B 17/07207 227/175.2 |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |

(56) References Cited

U.S. PATENT DOCUMENTS

| | | | |
|---|---|---|---|
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,157,145 B2 | 4/2012 | Shelton, IV et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,714,430 B2 * | 5/2014 | Natarajan ............ A61B 17/068 227/176.1 |
| 8,733,611 B2 | 5/2014 | Milliman |
| 2003/0111507 A1 | 6/2003 | Nunez |
| 2004/0073090 A1 | 4/2004 | Butler et al. |
| 2005/0023325 A1 * | 2/2005 | Gresham ............ A61B 17/115 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0144893 A1 * | 7/2006 | Lee .................... B25C 5/02 227/134 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0078808 A1 * | 4/2008 | Hess .................... A61B 17/105 227/181.1 |
| 2008/0300580 A1 * | 12/2008 | Shelton, IV ...... A61B 17/07207 606/1 |
| 2009/0090763 A1 * | 4/2009 | Zemlok ............ A61B 17/07207 227/175.2 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0051669 A1 * | 3/2010 | Milliman ............ A61B 17/115 227/175.2 |
| 2010/0069942 A1 * | 3/2010 | Shelton, IV ...... A61B 17/07207 606/170 |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |

(56) References Cited

U.S. PATENT DOCUMENTS

| | | |
|---|---|---|
| 2011/0114700 A1 | 5/2011 | Baxter, III et al. |
| 2011/0139852 A1* | 6/2011 | Zingman ............... A61B 17/072 227/176.1 |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0106418 A1* | 4/2016 | Shi ..................... A61B 17/1155 227/175.2 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0199089 A1* | 7/2016 | Hess ................. A61B 17/32001 227/180.1 |
| 2016/0302792 A1 | 10/2016 | Motai |
| 2017/0105736 A1* | 4/2017 | Chen .................. A61B 17/1155 |
| 2017/0319206 A1* | 11/2017 | Zhan ................. A61B 17/07207 |
| 2018/0028188 A1* | 2/2018 | Murugesan ........ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2010253280 A | 11/2010 |
| JP | 2011136169 A | 7/2011 |
| JP | 2013138860 A | 7/2013 |
| JP | 2015506223 A | 3/2015 |
| JP | 2015110062 A | 6/2015 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

OTHER PUBLICATIONS

European Search Report dated Aug. 5, 2019, issued in EP Appln. No. 16888757.

\* cited by examiner

CIRCULAR STAPLER WITH VISUAL INDICATOR MECHANISM

CROSS-REFERENCE TO RELATED APPLICATIONS

This application is a U.S. National Stage Application filed under 35 U.S.C. § 371(a) which claims the benefit of and priority of International Patent Application Serial No. PCT/CN2016/073471, filed Feb. 4, 2016, the entire disclosure of which is incorporated by reference herein.

BACKGROUND

1. Technical Field

The present disclosure relates to surgical stapling devices, and more particularly, to circular stapling devices that include visual indicator mechanisms for indicating when the surgical stapling device is in a fire-ready zone.

2. Background of Related Art

Anastomosis is the surgical joining of separate hollow organ sections. In known circular anastomosis procedures, two ends of organ sections are joined by means of a surgical stapling device that drives a circular array of staples through each organ section and simultaneously cores any tissue interior of the driven circular array of staples to free a tubular passage. Examples of such devices are described in U.S. Pat. Nos. 7,234,624, 6,945,444, 6,053,390, 5,568,579, 5,119,983, 4,646,745, 4,576,167, and 4,473,077, the content of each of which is incorporated herein by reference in its entirety.

Typically, a circular stapling device has an elongated shaft having a handle portion supported at a proximal end of the shaft and a staple cartridge supported at a distal end of the shaft. An anvil assembly including an anvil rod and an anvil head is also mounted to the distal end of the device. The anvil head is approximated in relation to the staple cartridge to clamp tissue between the staple cartridge and the anvil head of the anvil assembly.

Known surgical stapling devices include an indicator mechanism that provides an indication to a clinician that the anvil head of the anvil assembly has been moved into a firing zone in close approximation with a staple cartridge of the cartridge assembly. The firing zone is the zone of approximation in which the anvil head is positioned in close enough approximation with the staple cartridge to facilitate the proper formation of staples. Due to the small size of the staples being fired and, thus, the limited size of the firing zone, it can be difficult for a clinician to accurately identify using known visual indicator mechanisms exactly where the anvil head is in relation to the staple cartridge in the firing zone.

It would be advantageous to provide a surgical stapling device including a visual indicator mechanism capable of accurately identifying to a clinician the location of the anvil head within the firing zone during approximation of the anvil head and the staple cartridge.

SUMMARY

The presently disclosed visual indicator mechanism and surgical stapling device including such a visual indicator mechanism is provided to afford a clinician greater visualization of the movement of an anvil assembly in relation to a cartridge assembly after the anvil and cartridge assemblies have been approximated to within a firing zone, i.e., the zone of approximation in which the anvil head and staple cartridge are in close enough approximation to allow for the proper formation of staples against the anvil assembly. The visual indicator mechanism improves visualization of the different degrees of approximation within the firing zone by providing an indicator cover having spaced slots that allow indicia formed on an indicator member to sequentially appear within the spaced slots to identify the different degrees of approximation within the firing zone. Improving visualization of the position of the anvil head in relation to the staple cartridge of the cartridge assembly during approximation of the anvil head and staple cartridge within the firing zone allows the clinician to better control the degree of approximation to compensate for different tissue thicknesses.

In one aspect of the present disclosure, a surgical stapling device includes a handle assembly having a stationary handle defining a window and a firing trigger. A central body extends distally from the handle assembly. A cartridge assembly is supported on a distal end of the central body and an anvil assembly is supported on the distal end of the stapling device. An approximation mechanism includes a longitudinally movable drive screw that is operatively connected to the anvil assembly such that longitudinal movement of the drive screw between advanced and retracted positions effects movement of the anvil assembly in relation to the cartridge assembly between spaced and approximated positions. The drive screw supports an abutment. A visual indicator mechanism includes an indicator cover, an indicator and an indicator plate. The indicator cover is supported on the stationary handle above the window and defines a plurality of spaced slots. The indicator is positioned beneath the indicator cover adjacent the window and supports indicia. An indicator plate is movable from an advanced position to a retracted position within the stationary handle. The indicator plate supports a stop member and has a distal end connected to the indicator. The stop member is positioned to engage the abutment such that movement of the drive screw between the advanced and retracted positions effects movement of the indicator within the indicator cover between first and second positions, wherein the indicia are dimensioned and configured such that movement of the indicator within the indicator cover as the indicator plate is moved from the advanced position to the retracted position causes the indicia to become sequentially visible within the plurality of slots.

In embodiments, the visual indicator mechanism includes a biasing member supported within the stationary handle and positioned to urge the indicator plate towards the advanced position.

In embodiments, the indicia include a plurality of spaced colored bands.

In some embodiments, the plurality of slots includes first, second and third slots, and the plurality of spaced colored bands includes first, second, and third colored bands.

In certain embodiments, when the indicator is in the first position, the first colored band is spaced from the first slot a first distance, the second colored band is spaced from the second slot a second distance, and the third colored band is spaced from the third slot a third distance, wherein the first distance is greater than the second and third distances and the second distance is greater than the third distance.

In embodiments, the first colored band has a first width, the second colored band has a second width and the third colored band has a third width, the first width being less than the second and third widths and the second width being less than the third width.

In some embodiments, the indicator is pivotally supported beneath the indicator cover within the stationary handle.

In certain embodiments, the indicator plate includes a coupling member defining an elongated slot and the indicator includes an engagement member, the engagement member being received within the elongated slot to couple the indicator to the indicator plate.

In embodiments, the indicator plate includes a proximally extending portion and the stationary handle includes a bracket defining a cutout. The proximally extending portion extends through the cutout to guide movement of the indicator plate within the stationary handle.

In some embodiments, the biasing member is positioned in compression about the proximally extending portion between the bracket and a central portion of the indicator plate to urge the indicator plate in a distal direction.

In certain embodiments, the indicia include a stepped colored band and the plurality of slots includes first, second and third slots that are laterally and longitudinally spaced from each other.

In embodiments, the plurality of slots includes first, second and third slots, and the stepped colored band includes first, second, and third steps.

In some embodiments, when the indicator is in the first position, the first step of the colored band is spaced from the first slot a first distance, the second step of the colored band is spaced from the second slot a second distance, and the third step of the colored band is spaced from the third slot a third distance, wherein the first distance is greater than the first and second distances and the second distance is greater than the third distance.

BRIEF DESCRIPTION OF THE DRAWINGS

Various embodiments of a surgical stapling device including the presently disclosed visual indicator mechanism are described herein below with reference to the drawings, wherein:

FIG. 8 is a top, cutaway view of the handle assembly of a surgical stapling device as shown in FIG. 1 from above the indicator cover with the anvil head approximated into the firing zone to a minimum tissue gap;

DETAILED DESCRIPTION OF EMBODIMENTS

A surgical stapling device including embodiments of the presently disclosed visual indicator mechanism will now be described in detail with reference to the drawings in which like reference numerals designate identical or corresponding elements in each of the several views. In this description, the term "proximal" is used generally to refer to the portion of the device that is closer to a clinician, while the term "distal" is used generally to refer to the portion of the device that is farther from the clinician. In addition, the term "endoscopic" is used generally to refer to procedures including endoscopic, laparoscopic, and arthroscopic performed through a small incision or a cannula inserted into a patient's body. Finally, the term clinician is used generally to refer to medical personnel including doctors, nurses, and support personnel.

The presently disclosed visual indicator mechanism is provided to afford a clinician greater visualization of the movement of an anvil assembly in relation to a cartridge assembly after the anvil and firing assemblies have been approximated to within a firing zone, i.e., the zone of approximation in which the anvil head and staple cartridge are in close enough approximation to allow for the proper formation of staples against the anvil assembly. Improving visualization of the position of the anvil head in relation to the staple cartridge of the cartridge assembly during approximation of the anvil head and staple cartridge within the firing zone allows the clinician to better control the degree of approximation to compensate for different tissue thicknesses.

Figures 1, 2:
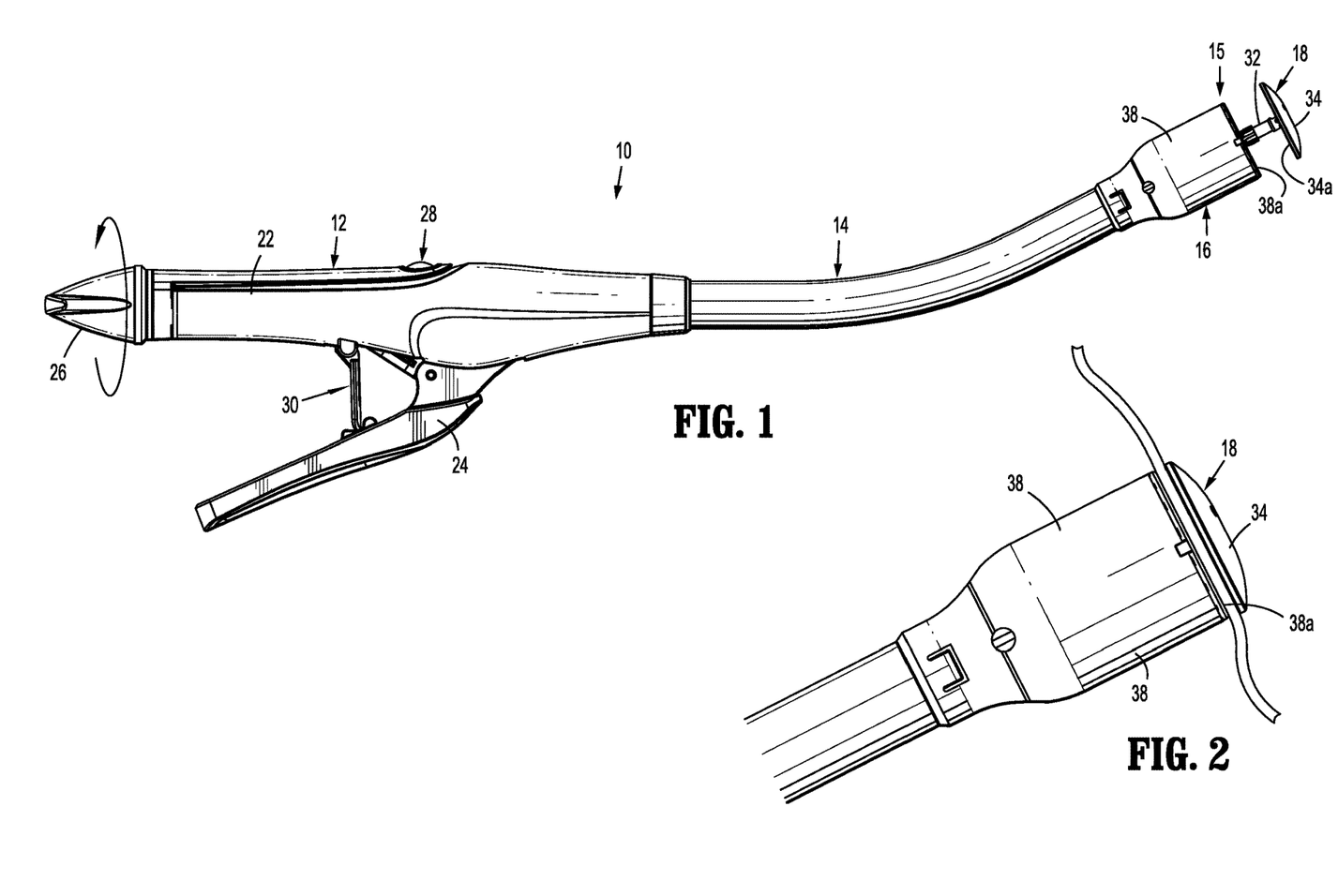
FIG. 1 is a perspective view of a surgical stapling device including one embodiment of the presently disclosed visual indicator mechanism with the end effector in an unapproximated position.
FIG. 2 is an enlarged view of the distal end of the surgical stapling device shown in FIG. 1 with the end effector in an approximated position and tissue clamped between an anvil head of the anvil assembly and the staple cartridge of a cartridge assembly.

FIGS. 1 and 2 illustrate one embodiment of a surgical stapling device 10 including one embodiment of the presently disclosed visual indicator mechanism as described in further detail below. Briefly, surgical stapling device 10 includes a handle assembly 12, a central body or elongated portion 14, and an end effector 15 including a shell or cartridge assembly 16 and an anvil assembly 18. Although the central body portion 14 is shown to be slightly curved, it is to be understood that the central body portion 14 can be straight or have any degree of curvature suitable to perform a desired surgical procedure.

Except where otherwise noted, the components of stapling device 10 are generally formed from thermoplastics including polycarbonates, and metals including stainless steel and aluminum. The particular material selected to form a particular component will depend upon the strength requirements of the particular component and upon whether the component is a reusable or disposable component. For example, the anvil assembly 18 may be formed from metal such as stainless steel, whereas portions of handle assembly 12 may be formed from thermoplastics such as a polycarbonate. In addition, the handle assembly 12 may be formed of an autoclavable material to allow for reuse whereas portions of the cartridge assembly may be formed of thermoplastics to allow for disposal. It is envisioned that other materials having the requisite strength requirements which are suitable for surgical use may be used to form the components of surgical stapling device 10.

Handle assembly 12 includes a stationary handle 22, a firing trigger 24, an approximation knob 26, a visual indictor mechanism or indicator assembly 28, and a lockout mechanism 30. The approximation knob 26 functions to retract and advance a drive screw 40 (FIG. 3) to advance or retract the anvil assembly 18 in relation to the cartridge assembly 16 between spaced and approximated positions as described below. The lockout mechanism 30 functions to prevent actuation of the firing trigger 24 until the cartridge and anvil assemblies 16, 18 have been approximated into a firing zone, i.e., the zone of approximation in which the anvil head and staple cartridge are in close enough approximation to allow for the proper formation of staples against the anvil assembly. During firing of the surgical stapling device 10, the firing trigger 24 functions to actuate a pusher (not shown) to eject staples from cartridge assembly 16 after the cartridge and anvil assemblies 16,18, respectively, have been approximated within the firing zone to form the staples against the anvil assembly 18.

Each of the components of handle assembly 12 identified above except for the indicator assembly 28 which is described in detail below, is substantially as described in U.S. Pat. No. 7,303,106 ("the '106 Patent") which is incorporated herein by reference in its entirety. Only those components of the handle assembly 12 that interact with the presently disclosed indicator assembly 28 will be described in further detail herein.

The anvil assembly 18 includes an anvil shaft or center rod 32 and an anvil head 34. In embodiments, the anvil head 34 is pivotally mounted to the distal end of anvil shaft 32 such that the anvil head 34 can move between an operative non-tilted position and a tilted reduced profile position (not shown). Such an anvil assembly 18 is described in detail in the '106 Patent. Alternately, the anvil assembly 18 may include an anvil head 34 that is fixedly secured to the anvil center rod 32. The anvil head 34 supports an anvil plate 34a that includes a plurality of staple forming depressions (not shown) and is movable into close approximation with the cartridge assembly 16 to deform staples ejected from the cartridge assembly 16.

The cartridge assembly 16 is secured to the distal end of central body portion 14 of the surgical stapler 10 and includes a shell or housing 38. The housing 38 supports a pusher back (not shown), a knife (not shown), and a staple cartridge 38a (FIG. 1) that supports one or more annular arrays of staples (not shown). Details of the components of the cartridge assembly 16 are also provided in the '106 Patent.

Figure 3:
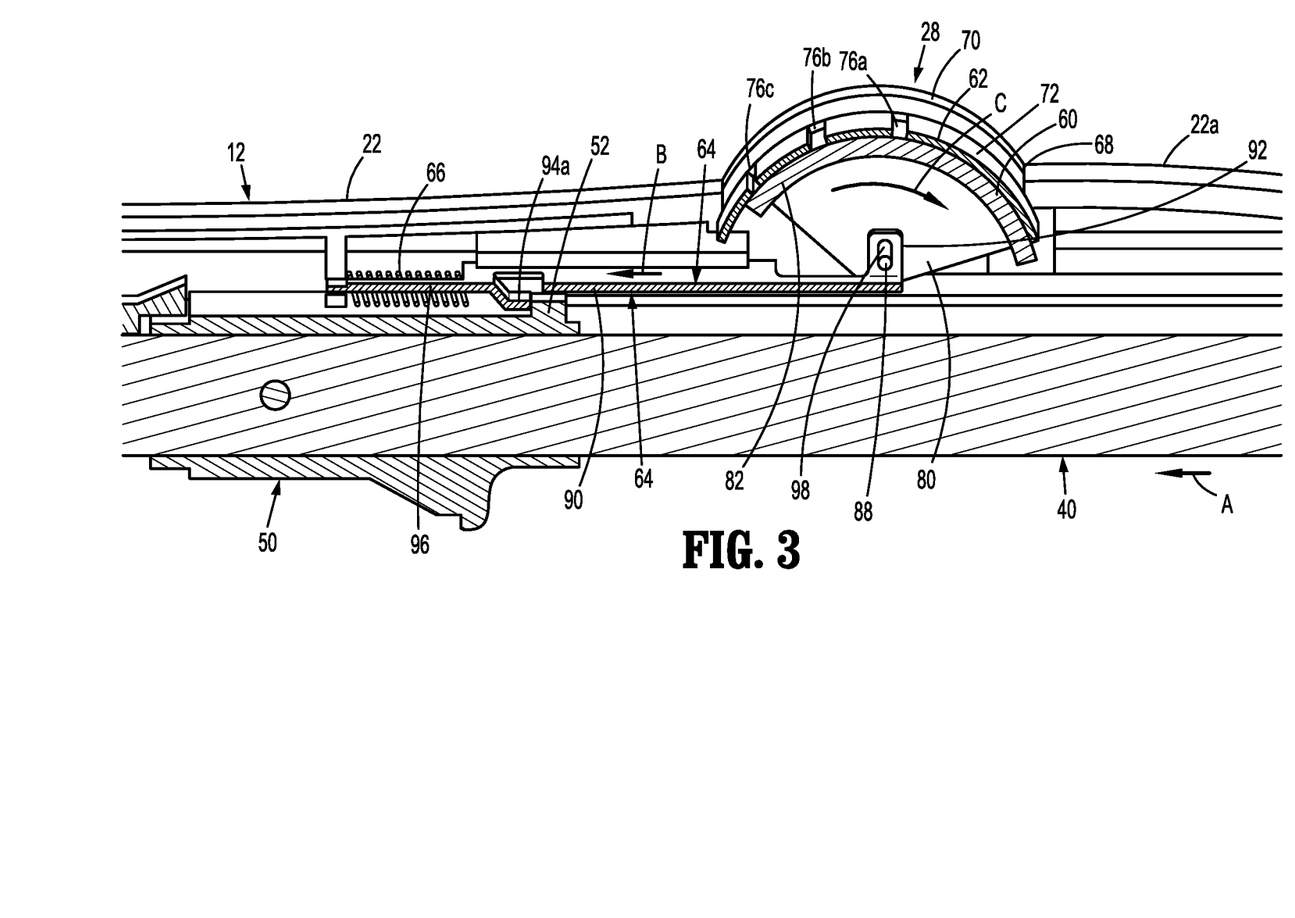
FIG. 3 is a side view of the handle assembly of the surgical stapling device shown in FIG. 1 with a handle half-section removed illustrating the visual indicator mechanism.

Referring also to FIG. 3, the anvil assembly 18 is supported on the distal end of an approximation mechanism (not shown in its entirety) that includes the rotation knob 26, an anvil retainer (not shown) and the drive screw 40 (FIG. 3). The rotation knob 26 is operably coupled to a proximal end of the drive screw 40 and the anvil retainer (not shown) is coupled to a distal end of the drive screw 40 such that actuation of the rotation knob 26 retracts and advances the drive screw 40 within the stationary handle 22 to move the anvil assembly 18 in relation to the cartridge assembly 16 between the spaced position (FIG. 1) and the approximated position (FIG. 2). A screw stop 50 is fixedly supported on the drive screw 40 and includes an abutment 52 as described in further detail below. Further details of the approximation mechanism are provided in the '106 patent.

The rotation knob 26 is manually rotated to approximate the anvil assembly 18 and the cartridge assembly 16. More specifically, when the rotation knob 26 is manually rotated in a first direction, the drive screw 40 is moved proximally within the stationary handle 22 from an advanced position towards a retracted position. As discussed above, the lockout mechanism 30 prevents actuation of the firing trigger 24 through an actuation stroke until the anvil assembly 18 is closely approximated with the cartridge assembly 16 to within the firing zone. After the cartridge assembly 16 and the anvil assembly 18 are approximated to within the firing zone, the tissue gap defined between the anvil assembly 18 and the cartridge assembly 16 is further adjustable to accommodate tissues of different thicknesses as described in further detail below.

Figure 4:
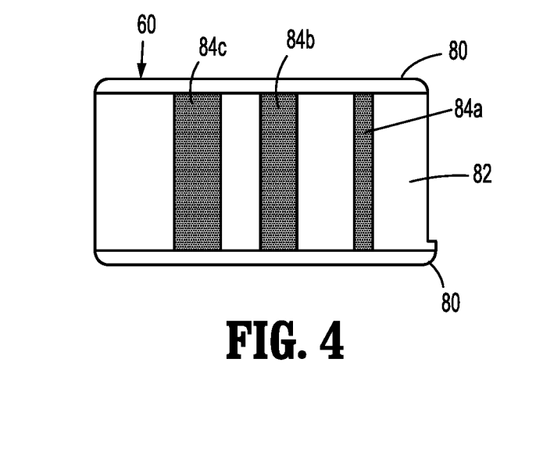
FIG. 4 is a top view of the indicator of the visual indicator mechanism shown in FIG. 3A.

Referring to FIGS. 3-4, the indicator assembly 28 includes an indicator 60, an indicator cover 62, an indicator plate 64 and a biasing member 66. The indicator cover 62 is positioned over an opening or window 68 defined in an upper surface 22a of the stationary handle 22 and includes a pair of sidewalls 70, a curved upper wall 72 supported on the upper edge of the sidewalls 70 and an open bottom 74. The curved upper wall 72 is positioned above the upper surface 22a of the stationary handle 22 and defines three spaced slots 76a-c that allow for visualization of the indicator 60 within the stationary handle 22 as described in further detail below.

Figure 3A:
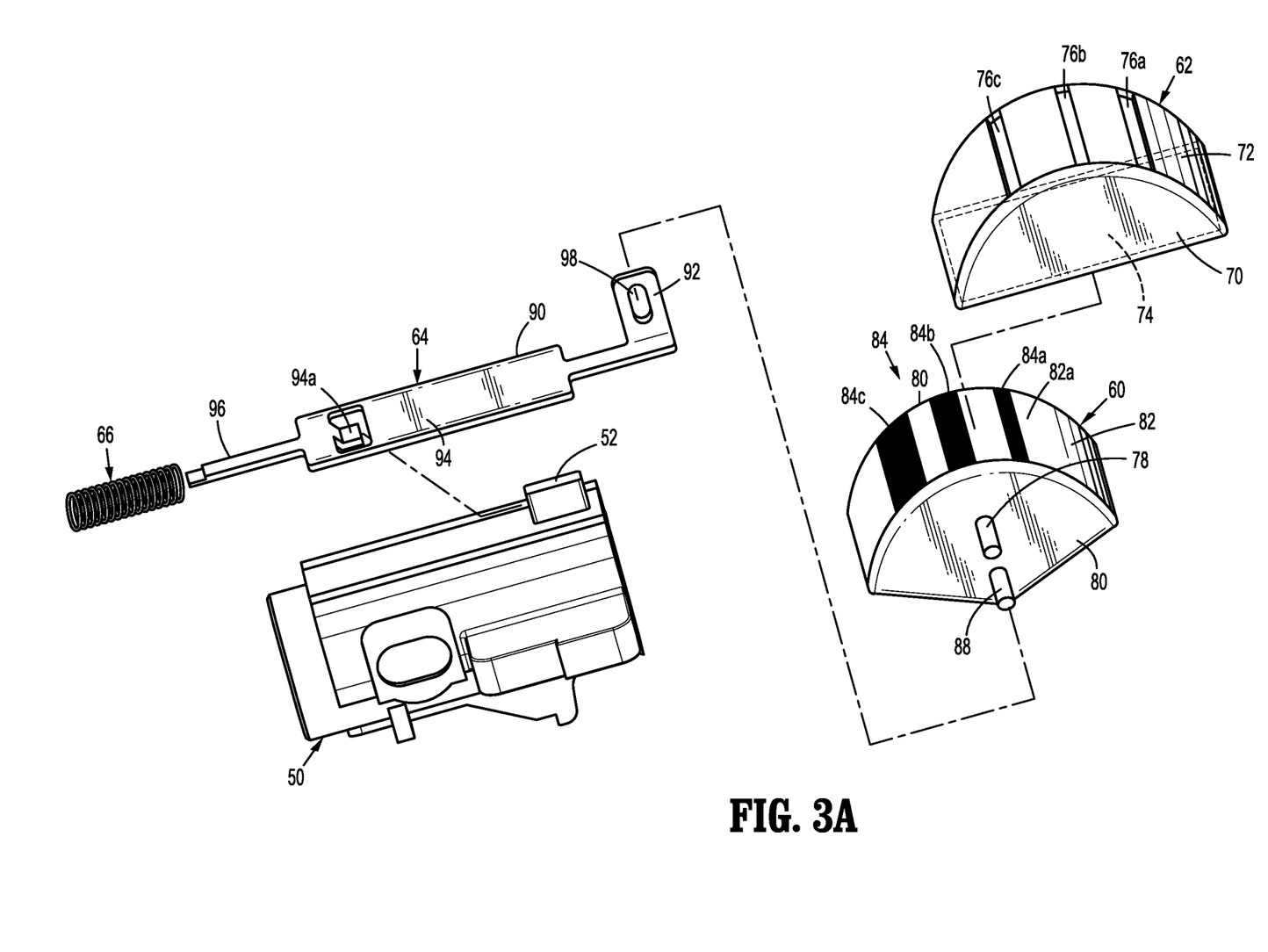
FIG. 3A is a side, perspective, exploded view of the visual indicator mechanism of the surgical stapling device shown in FIG. 1.

The indicator 60 has a shape that corresponds to the shape of the indicator cover 62 and is pivotally supported within the window 68 of the stationary handle 22 (FIG. 1) beneath the indicator cover 62 about a pivot member 78. More specifically, the indicator 60 includes a pair of spaced sidewalls 80 and a curved upper wall 82 supported on the top edge of the sidewalls 80. The curved upper wall 82 includes an upper surface 82a (FIG. 3A) that supports indicia 84. In embodiments, the indicia 84 include three colored stripes or bands 84a-c. Alternately, other types of indicia may be used including symbols, letters, and/or numbers. The indicator 60 is pivotally supported within the indicator cover 62 on a pivot member 78. One of the sidewalls 80 of the indicator 60 supports an engagement member 88 (FIG. 3A) that is described in further detail below.

In embodiments, the indicator plate 64 includes a body 90 having a distal end defining a coupling member 92, a central portion 94 defining a stop surface 94a, and a proximal end including a proximally extending finger 96. The stop surface 94a is positioned to engage the abutment 52 on the screw stop 50 when the drive screw 40 is retracted within the stationary handle 22 to approximate the cartridge and anvil assemblies 16, 18. The indicator plate 64 is slidably supported within the stationary handle 22, e.g., along grooves defined along inner walls of the stationary handle 22. The coupling member 92 defines a vertically extending elongated slot 98 that receives the engagement member 88 of the indicator 60 and the finger 96 of the indicator plate 64 extends through a bracket 100 defining a cutout 100a defined within the stationary housing 22 to guide movement of the indicator plate 64 between advanced and retracted positions. The biasing member 66, which may be a coil spring, is positioned about the finger 96 between the distal end of the bracket 100 and the proximal end of the central portion 94 of the indicator plate 64 to urge the indicator plate 64 towards the advanced position.

In use, when the rotation knob 26 (FIG. 1) is rotated to move the drive screw 40 in the direction indicated by arrow "A" in FIG. 3 towards its retracted position to move the anvil assembly 18 towards the cartridge assembly 16, the abutment 52 on the screw stop 50 moves into engagement with the stop member 94a on the indicator plate 64 to pull the indicator plate 64 proximally with the drive screw 40 in the direction indicated by arrow "B" in FIG. 3 against the force of the biasing member 66. As the indicator plate 64 is moved from its advanced position towards its retracted position in the direction indicated by arrow "B", the coupling member 92 of the indicator plate 64 pulls the engagement member 88 of the indicator 60 to pivot the indicator 60 in the direction indicted by arrow "C" in FIG. 3.

Figure 5:
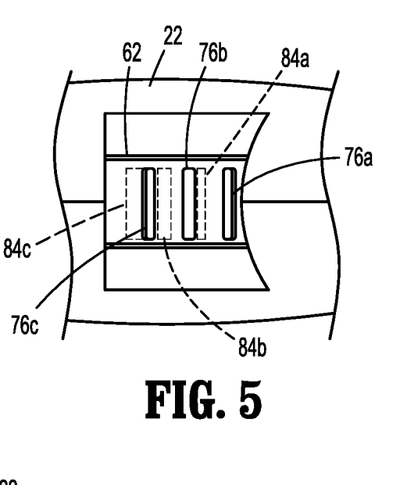
FIG. 5 is a top, cutaway view of the handle assembly of the surgical stapling device shown in FIG. 1 from above the indicator cover prior to approximation of the anvil head into the firing zone showing colored bands of the indicator in phantom.
Figure 6:
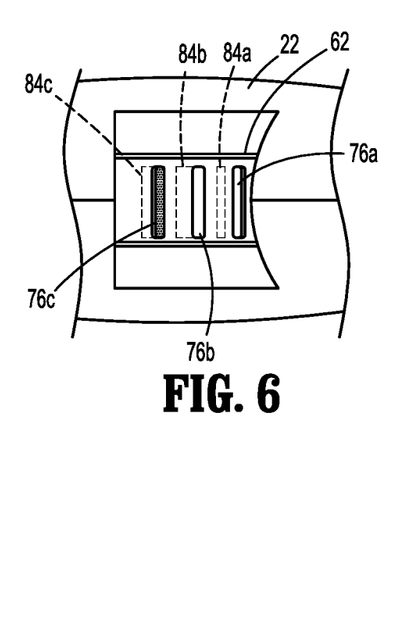
FIG. 6 is a top, cutaway view of the handle assembly of the surgical stapling device shown in FIG. 1 from above the indicator cover with the anvil head approximated into the firing zone to a maximum tissue gap.
Figure 7:
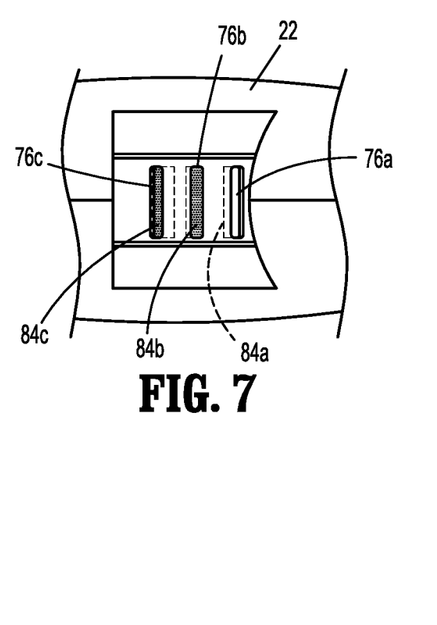
FIG. 7 is a top, cutaway view of the handle assembly of the surgical stapling device shown in FIG. 1 from above the indicator cover with the anvil head approximated into the firing zone to an intermediate tissue gap.
Figure 8:
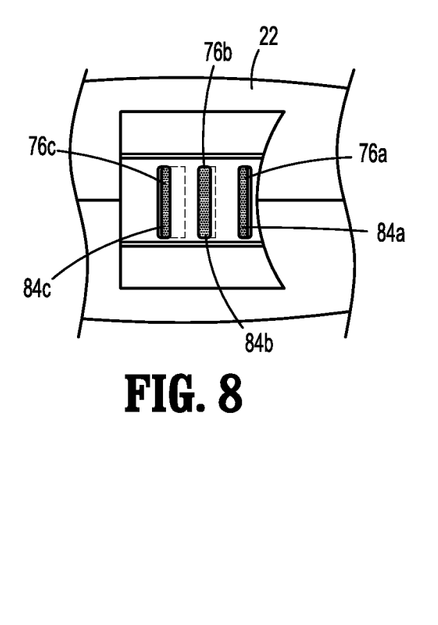
FIG. 8 is a top, cutaway view of the handle assembly of the surgical stapling device shown in FIG. 1 from above the indicator cover with the anvil head approximated into the firing zone to a minimum tissue gap.

Referring to FIG. 5, prior to approximation of the cartridge and anvil assemblies 16, 18 into the firing zone, each of the colored bands 84a-c of the indicator 60 is positioned adjacent a respective one of the slots 76a-c of the indicator cover 62. As shown in FIG. 5, when the indicator 60 is in its non-actuated position prior to pivotal movement by the indicator plate 64, the distance between the colored band 84c and the slot 76c is less than the distance between the colored band 84b and the slot 76b, and the distance between the colored band 84b and the slot 76b is less than the distance between the colored band 84a and the slot 76a. As such, when the indicator 60 is pivoted in the direction indicated by arrow "C" in FIG. 3 into the firing zone, the colored band 84c will appear in the slot 76c prior to the colored bands 84b and 84a appearing in slots 76b and 76a. When the colored band 84c appears in the slot 76c, this indicates to a clinician that the anvil head 34 of the anvil assembly 18 has been approximated in relation to the staple cartridge 38a (FIG. 2) to a maximum gap position in the firing zone. The maximum gap position in the firing zone is the position in which the anvil head 34 and the staple cartridge 38a define the largest tissue gap in the firing zone and is suitable for treating relatively thick tissue.

When the drive screw 40 is retracted further in the direction indicated by arrow "A" in FIG. 3, the abutment 52 of the screw stop 50 continues to pull the indicator plate 64 proximally against the force of the biasing member 66 to further pivot the indicator 60 in the direction indicated by arrow "C" in FIG. 3. As the indicator 60 continues to pivot, the colored band 84c, which is thicker than bands 84a and 84b, remains visible through slot 76c and the colored band 84b appears in the slot 76b. The colored band 84a, which is thinner than colored band 84b, approaches slot 76a but is not yet visible through slot 76a. When the colored band 84b appears in the slot 76b, this indicates to a clinician that the anvil head 34 of the anvil assembly 18 has been approximated to an intermediate gap position smaller than the maximum gap position in the firing zone. The intermediate gap position in the firing zone is suitable for treating tissue of intermediate thickness.

When the drive screw 40 is retracted further in the direction indicated by arrow "A" in FIG. 3 to its fully retracted position, the abutment 52 of the screw stop 50 continues to pull the indicator plate 64 proximally against the force of the biasing member 66 to further pivot the indicator 60 in the direction indicated by arrow "C" in FIG. 3. As the indicator continues to pivot, the colored band 84c and 84b which are thicker than band 84a remain visible through slots 76c and 76b and the colored band 84a appears in the slot 76a. When the colored band 84a appears in the slot 76a, this indicates to a clinician that the anvil head 34 of the anvil assembly 18 has been approximated to a minimum gap position smaller than the intermediate tissue gap in the firing zone. The minimum gap position in the firing zone is suitable for treating tissue of relatively small thicknesses.

As discussed above, the colored bands 84a-c may have different thicknesses. More specifically, to ensure that the colored band 84c remains visible under slot 76c and that the colored band 84b remains visible under slot 76b as the indicator 60 is pivoted through the firing zone, the colored band 84c may have a thickness greater than colored bands 84b and 84a, and the colored band 84b may have a thickness greater than the thickness of colored band 84a.

FIGS. 9-12 illustrate another embodiment of the presently disclosed visual indicator assembly shown generally as 128. Indicator assembly 128 is substantially the same as indicator assembly 28 except that the configuration of the slots 176a-c and the configuration of the indicia 84 has been changed. More specifically, the indicator cover 162 of the indicator assembly 128 includes slots 176a-c that are longitudinally and laterally offset from each other and the indicator 160 includes a single stepped colored band 184 having three steps 184a-c. Each of the steps 184a-c of the colored band 184 is laterally aligned with a respective one of the slots 176a-c.

Figure 9:
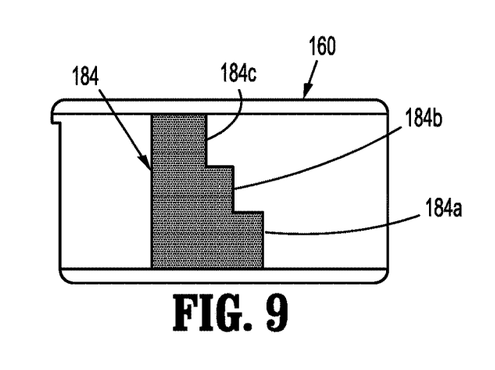
FIG. 9 is a top view of the indicator of another embodiment of the presently disclosed visual indicator mechanism.
Figure 10:
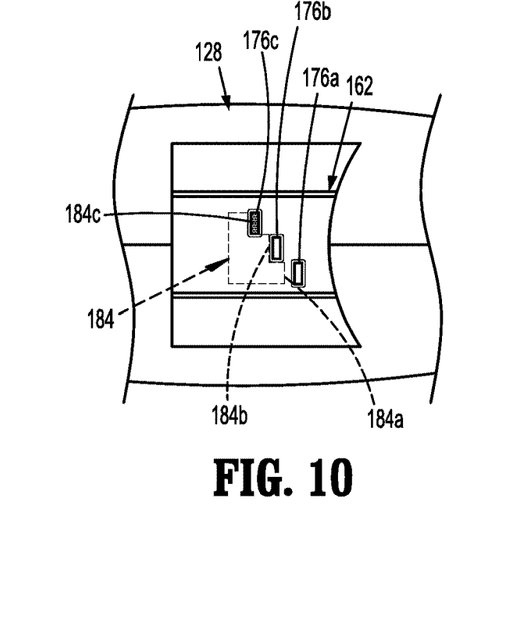
FIG. 10 is a top, cutaway view of the handle assembly of a surgical stapling device as shown in FIG. 1 including the visual indicator mechanism of FIG. 9 from above the indicator cover the anvil head approximated into the firing zone to a maximum tissue gap.
Figure 11:
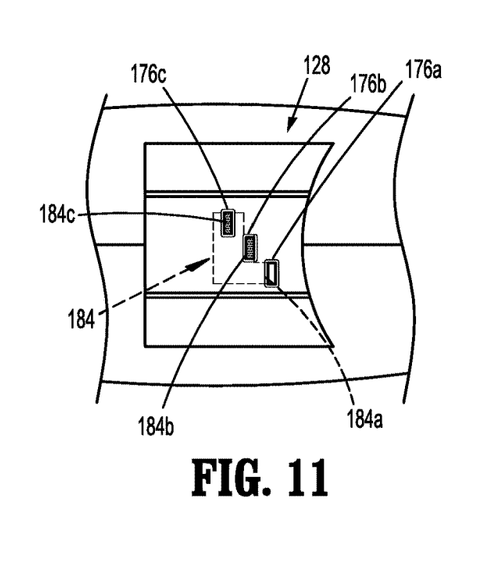
FIG. 11 is a top, cutaway view of the handle assembly of a surgical stapling device as shown in FIG. 1 from above the indicator cover with the anvil head approximated into the firing zone to an intermediate tissue gap.
Figure 12:
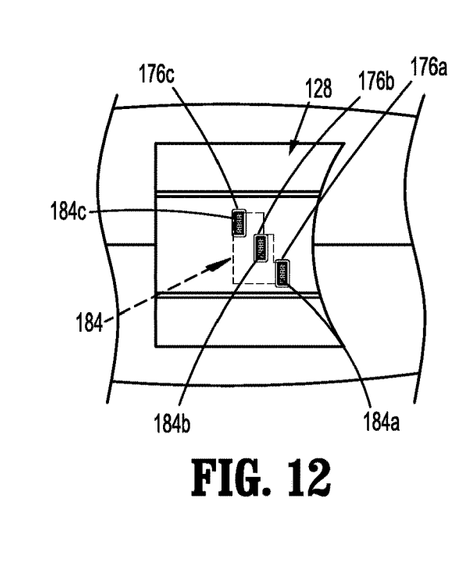

As shown in FIGS. 9 and 10, the distance between the step 184c of the colored band 184 and the slot 176c is less than the distance between the step 184b of the colored band 184 and the slot 176b and the distance between the step 184b and the colored band 184 and the slot 176b is less than the distance between the step 184a of the colored band 184 and the slot 176a. As such, when the indicator 60 is pivoted in the direction indicated by arrow "C" in FIG. 3 into the firing zone, the step 184c of the colored band 184 will appear in the slot 176c prior to the steps 184b and 184a of colored bands 184 appearing in slots 176b and 176a, respectively. Similarly, the step 184b of the colored band 184 will appear in the slot 176b prior to the step 184a of colored band 184 appearing in slot 176a.

Operation of the indicator assembly 128 is substantially as described above in regard to indicator assembly 28. As such, no further description of the indicator assembly 128 is provided herein.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
    a handle assembly including a stationary handle and a firing trigger, the stationary handle defining a window;
    a central body extending distally from the handle assembly;
    a cartridge assembly supported on a distal end of the central body;
    an anvil assembly;
    an approximation mechanism including a longitudinally movable drive screw, the drive screw being operatively connected to the anvil assembly such that longitudinal movement of the drive screw between advanced and retracted positions effects movement of the anvil assembly in relation to the cartridge assembly between spaced and approximated positions, the drive screw supporting an abutment; and
    a visual indicator mechanism including an indicator cover, an indicator and an indicator plate, the indicator cover being supported on the stationary handle above the window and defining a plurality of spaced slots, the indicator being positioned beneath the indicator cover adjacent the window, the indicator supporting indicia, and the indicator plate movable from an advanced position to a retracted position within the stationary handle, the indicator plate supporting a stop member and having a distal end connected to the indicator, wherein the stop member is positioned to engage the abutment such that movement of the drive screw between the advanced and retracted positions effects movement of the indicator within the indicator cover between first and second positions, wherein the indicia are dimensioned and configured such that movement of the indicator within the indicator cover as the indicator plate is moved from the advanced position to the retracted position causes the indicia to become sequentially visible within the plurality of slots such that the indicia is visible in all of the plurality of spaced slots when the indicator plate is in its retracted position, and wherein positioning of the indicia within a first slot of the plurality of slots indicates that the anvil assembly has been approximated in relation to the cartridge assembly to define a maximum tissue gap within a firing zone, positioning of the indicia within a second slot of the plurality of slots indicates that the anvil assembly has been approximated in relation to the cartridge assembly to define an intermediate tissue gap within the firing zone, and positioning of the indicia within a third slot of the plurality of slots indicates that the anvil assembly has been approximated in relation to the cartridge assembly to define a minimum tissue gap within a firing zone.

2. The surgical stapling device according to claim 1, further including a biasing member supported within the stationary handle and positioned to urge the indicator plate towards the advanced position.

3. The surgical stapling device according to claim 1, wherein the indicia include a plurality of spaced colored bands.

4. The surgical stapling device according to claim 3, wherein the plurality of spaced colored bands includes first, second, and third colored bands.

5. The surgical stapling device according to claim 4, wherein when the indicator is in the first position, the first colored band is spaced from the first slot a first distance, the second colored band is spaced from the second slot a second distance, and the third colored band is spaced from the third slot a third distance, the first distance being greater than the first and second distances and the second distance being greater than the third distance.

6. The surgical stapling device according to claim 5, wherein the first colored band has a first width, the second colored band has a second width and the third colored band has a third width, the first width being less than the second and third widths and the second width being less than the third width.

7. The surgical stapling device according to claim 1, wherein the indicator is pivotally supported beneath the indicator cover within the stationary handle.

8. The surgical stapling device according to claim 1, wherein the indicator plate includes a coupling member defining an elongated slot and the indicator includes an engagement member, the engagement member received within the elongated slot to couple the indicator to the indicator plate.

9. The surgical stapling device according to claim 1, wherein the indicator plate includes a proximally extending portion and the stationary handle includes a bracket defining a cutout, the proximally extending portion extending through the cutout to guide movement of the indicator plate within the stationary handle.

10. The surgical stapling device according to claim 9, wherein the biasing member is positioned in compression about the proximally extending portion between the bracket and a central portion of the indicator plate to urge the indicator plate in a distal direction.

11. The surgical stapling device according to claim 1, wherein the indicia include a stepped colored band.

12. The surgical stapling device according to claim 11, wherein the plurality of slots are laterally and longitudinally spaced from each other.

13. The surgical stapling device according to claim 12, wherein the stepped colored band includes first, second, and third steps.

14. The surgical stapling device according to claim 13, wherein when the indicator is in the first position, the first step of the colored band is spaced from the first slot a first distance, the second step of the colored band is spaced from the second slot a second distance, and the third step of the colored band is spaced from the third slot a third distance, the first distance being greater than the first and second distances and the second distance being greater than the third distance.

* * * * *